US009724060B2

(12) United States Patent
Kühn et al.

(10) Patent No.: US 9,724,060 B2
(45) Date of Patent: Aug. 8, 2017

(54) CT APPARATUS WITH COOLING SYSTEM

(71) Applicant: Siemens Aktiengesellschaft, Munich (DE)

(72) Inventors: Ulrich Kühn, Baiersdorf (DE); Christian Willming, Forchheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 118 days.

(21) Appl. No.: 14/666,419

(22) Filed: Mar. 24, 2015

(65) Prior Publication Data

US 2015/0272525 A1    Oct. 1, 2015

(30) Foreign Application Priority Data

Mar. 27, 2014    (DE) .................. 10 2014 205 739

(51) Int. Cl.
*A61B 6/03* (2006.01)
*H05G 1/02* (2006.01)
(Continued)

(52) U.S. Cl.
CPC .............. *A61B 6/4488* (2013.01); *A61B 6/44* (2013.01); *F28F 9/0263* (2013.01);
(Continued)

(58) Field of Classification Search
CPC .... A61B 6/00; A61B 6/02; A61B 6/03; A61B 6/032; A61B 6/035; A61B 6/44; A61B 6/4447; A61B 6/4488; A61B 50/00; A61B 50/001; A61B 50/0014; A61B 2560/00; A61B 2560/04; A61B 2560/0406;
(Continued)

(56) References Cited

U.S. PATENT DOCUMENTS 4,969,167 A * 11/1990 Zupancic ............... A61B 6/035
378/10
5,761,269 A *  6/1998 Sugihara ............. A61B 6/4488
378/199
(Continued)

FOREIGN PATENT DOCUMENTS

CN    1541619 A    11/2004
DE    10304661 A1    12/2004
(Continued)

OTHER PUBLICATIONS

German Search Report dated Dec. 5, 2014 issued in corresponding German Application No. 102014205739.6.
(Continued)

*Primary Examiner* — Anastasia Midkiff
(74) *Attorney, Agent, or Firm* — Harness, Dickey & Pierce, P.L.C.

(57) ABSTRACT

A CT system is disclosed for generating tomographic recordings of an examination object. In an embodiment, the CT system includes at least a gantry with a rotatable support for receiving components of the CT system, and a cooling system for cooling the components secured to the gantry with at least one air duct. In at least one embodiment, an incoming-air duct of the cooling system is divided into at least two segments to ensure uniform pressure distribution in the incoming-air duct.

16 Claims, 4 Drawing Sheets

(51) Int. Cl.
F28F 9/02 (2006.01)
A61B 6/00 (2006.01)
H01L 23/467 (2006.01)

(52) U.S. Cl.
CPC .......... F28F 9/0265 (2013.01); F28F 9/0282 (2013.01); H05G 1/025 (2013.01); A61B 6/035 (2013.01); A61B 2560/04 (2013.01); A61B 2560/0406 (2013.01); F28F 9/026 (2013.01); H01L 23/467 (2013.01); H05G 1/02 (2013.01)

(58) Field of Classification Search
CPC . H05G 1/00; H05G 1/02; H05G 1/025; A61N 5/002; A61N 5/005; F01P 1/00; E04F 17/04; F28F 9/026; F28F 9/0263; F28F 9/0265; F28F 9/0268; F28F 9/0282; H01L 23/46; H01L 23/467; F23M 5/00; F23M 5/08; F23M 5/085
See application file for complete search history.

(56) References Cited

U.S. PATENT DOCUMENTS

| | | | |
|---|---|---|---|
| 6,453,010 B1 | 9/2002 | Miller et al. | |
| 6,909,775 B2* | 6/2005 | Ray | A61B 6/4488 378/141 |
| 7,851,765 B2* | 12/2010 | Heismann | A61B 6/035 250/370.15 |
| 7,887,237 B2* | 2/2011 | Krug | A61B 6/4488 378/199 |
| 2004/0202287 A1 | 10/2004 | Muller | |
| 2004/0228450 A1 | 11/2004 | Mueller | |
| 2007/0053500 A1 | 3/2007 | Distler et al. | |
| 2007/0053501 A1 | 3/2007 | Distler et al. | |
| 2009/0279660 A1* | 11/2009 | Takamatsu | A61B 6/035 378/19 |
| 2010/0322374 A1 | 12/2010 | Buettner et al. | |
| 2011/0228910 A1* | 9/2011 | Gregerson | A61B 6/4488 378/200 |

FOREIGN PATENT DOCUMENTS

| | | |
|---|---|---|
| DE | 60131117 T2 | 8/2008 |
| DE | 102005041542 B4 | 9/2008 |
| DE | 102005041538 B4 | 4/2009 |

OTHER PUBLICATIONS

Office Action for Corresponding Chinese Patent Application No. 201510134766.3 dated Mar. 3, 2017 and English language translation thereof.

* cited by examiner

Section A-A

Section B-B

Section B-B

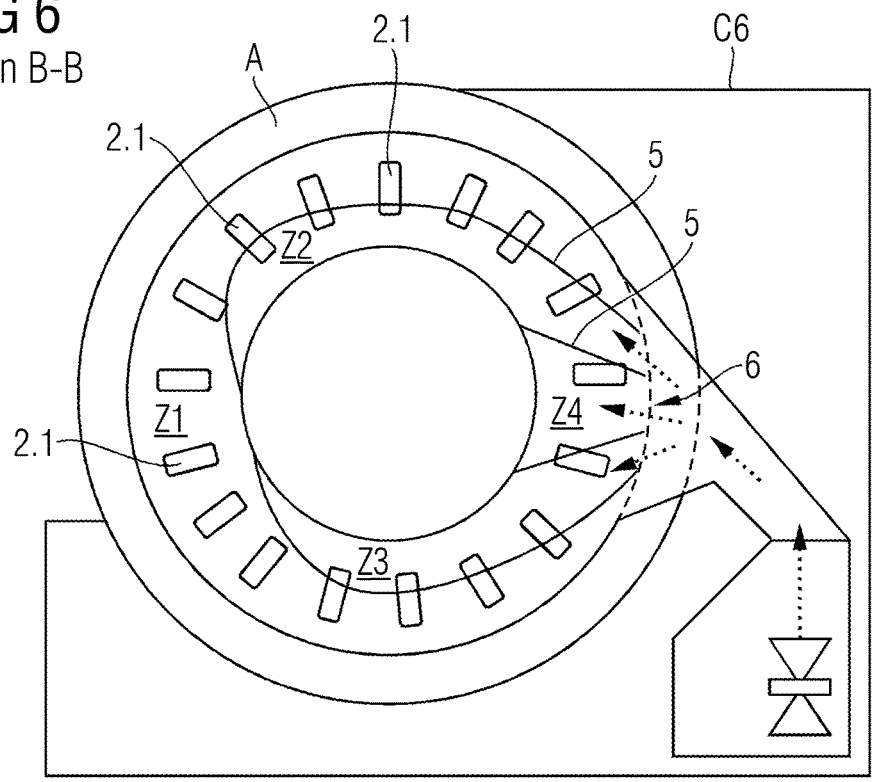
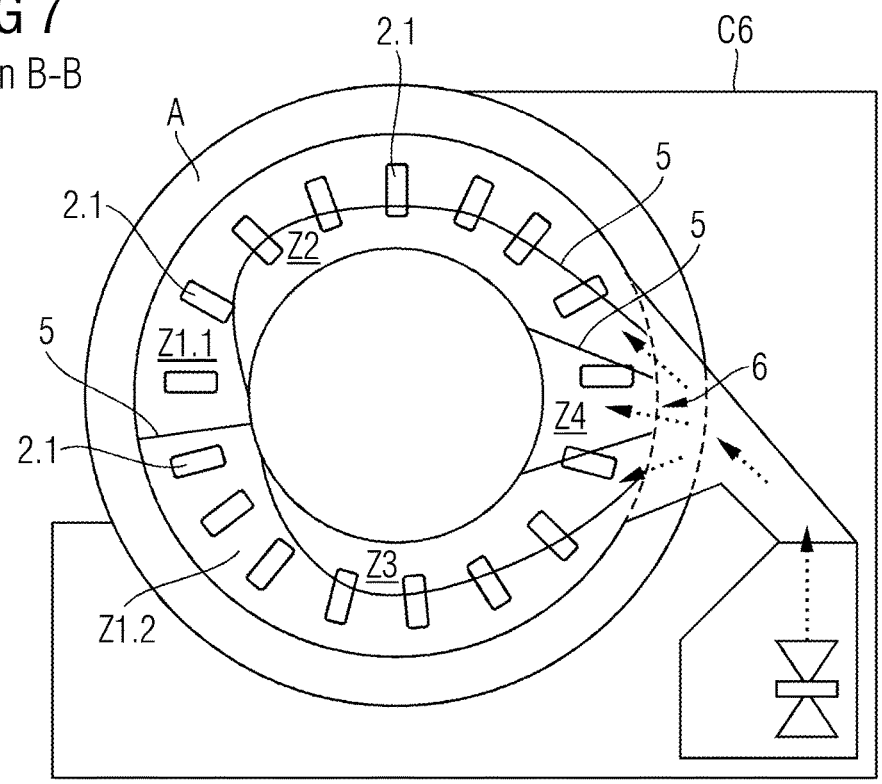

CT APPARATUS WITH COOLING SYSTEM

PRIORITY STATEMENT

The present application hereby claims priority under 35 U.S.C. §119 to German patent application number DE 102014205739.6 filed Mar. 27, 2014, the entire contents of which are hereby incorporated herein by reference.

FIELD

At least one embodiment of the invention generally relates to a CT system for generating tomographic recordings of an examination object, at least having a gantry with a rotatable support for receiving components of the CT system, and a cooling system for cooling the components secured to the gantry with at least one air duct.

BACKGROUND

During operation, the system components arranged on the gantry of a CT system produce between 12 kW and 17 kW of heat. In an X-ray tube of the CT system, by way of example, the majority of the energy used is converted into heat during generation of X-ray radiation. This heat must be removed from the gantry in order to protect the system components, in particular a radiator-detector system. For this purpose it is necessary to supply the system components on the rotating support with sufficient cooling air at all times.

It is known to cool individual components with additional fans attached to the rotating support. These fans are very susceptible to the accelerations during rotation of the support, however. These additional fans are therefore often omitted for reliability reasons, in order to avoid maintenance. However, in this case the uniform air supply of the components, viewed over the circumference of the gantry, cannot always be ensured. Temperature problems can therefore occur when the support is stationary since the waste heat cannot be adequately removed.

It is also known to locally correct the pressure by way of baffles in the incoming-air ducts and an adjustment of the air outlets out of the incoming-air duct to the components in order to generate an optimally uniform pressure in the incoming-air duct and thus ensure optimally uniform cooling along the circumference of the gantry.

In the case of non-uniform cooling along the circumference, in particular during operation when the gantry is stationary, it is also necessary to operate the gantry cooling at a higher power. A higher noise level is also generated therewith, however.

SUMMARY

At least one embodiment of the invention is directed to an improved cooling system for a gantry of a CT system which enables uniform and reliable cooling of the gantry and the system components located thereon, primarily also when the support is stationary.

Advantageous developments of the invention are the subject matter of subordinate claims.

In at least one embodiment, the CT system includes at least a gantry with a rotatable support for receiving components of the CT system, and a cooling system for cooling the components secured to the gantry with at least one air duct such that an incoming-air duct of the cooling system is divided into at least two segments to ensure a uniform pressure distribution in the incoming-air duct.

BRIEF DESCRIPTION OF THE DRAWINGS

The invention will be described in more detail below with reference to preferred example embodiments and with the aid of the figures, wherein only features necessary for an understanding of the invention are illustrated. The following reference characters are used: 1: support; 2.1: air inlet; 2.2: air outlet; 3: gantry interior; 4: baffle; 5: partition; 6: inlet opening; A: waste-air duct; C1: CT system; C2: first X-ray tube; C3: first detector; C4: second X-ray tube (optional); C5: second detector (optional); C6: gantry housing; C7: patient; C8: examination table; C9: system axis; C10: arithmetic and control unit; Prg1 to Prgn: computer programs; Z: incoming-air duct; Z1.1, Z1.2 to Z4: segments of the incoming-air duct.

In detail in the drawings:

FIG. 6: shows a schematic view of the gantry according to FIG. 2 with a further embodiment of an inventive air circuit along the plane of intersection B-B, and FIG. 7: shows a schematic view of the gantry according to FIG. 2 with yet a further embodiment of an inventive air circuit along the plane of intersection B-B.

DETAILED DESCRIPTION OF THE EXAMPLE EMBODIMENTS

Figure 1:
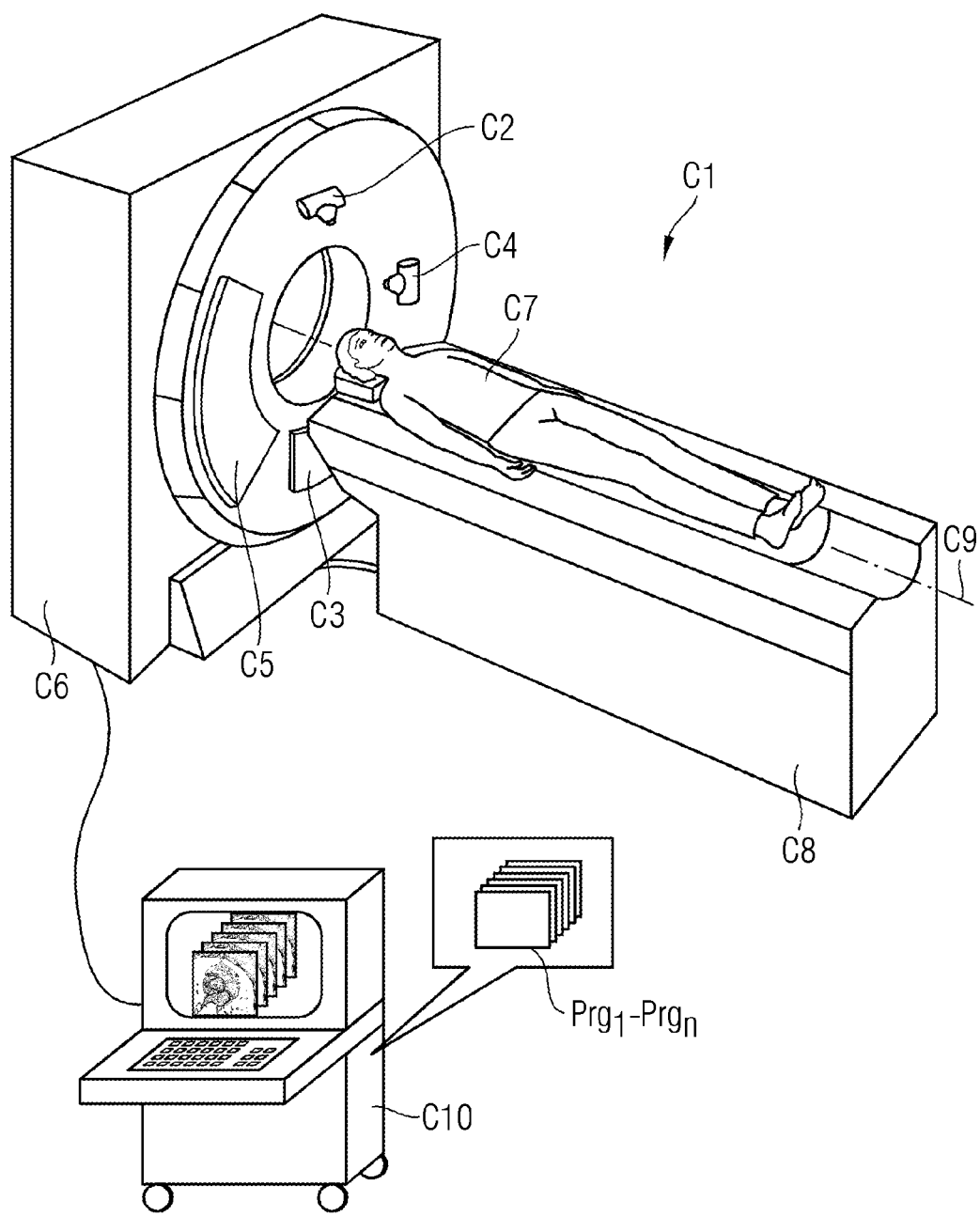
FIG. 1: shows a schematic view of a CT system with arithmetic unit.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventors recognized that by dividing the incoming-air duct into a plurality of segments, which can be individually supplied with air and in which the pressure can therefore be individually adjusted, a uniform pressure can be achieved in the incoming-air duct. The uniform pressure in turn enables uniform and position-independent cooling of the system components along the circumference of the gantry. This is ensured even when the support is stationary. The individual segments of the incoming-air duct are supplied with cooling air centrally and are decoupled from each other as a result, so there are no interactions between the segments. The segments of the incoming-air duct are connected to the waste-air duct by the components to be cooled.

By segmenting the incoming-air duct a pressure and volume flow can be easily and reliably adjusted for all regions along the circumference of the gantry. The pressure in the individual segments can consequently be adapted to each other, resulting in a uniform or consistent pressure distribution. The cooling of the system components along the circumference of the gantry is no longer position-dependent therefore when the support is stationary. Cooling is consequently reliable even when the support is stationary.

The cooling system can also be operated with less power so the noise level is reduced in the incoming-air ducts compared to the known solution with baffles.

The inventors accordingly propose improving a CT system for generating tomographic recordings of an examination object, in particular a patient. In at least one embodiment, the CT system includes at least a gantry with a rotatable support for receiving components of the CT system, and a cooling system for cooling the components secured to the gantry with at least one air duct such that an incoming-air duct of the cooling system is divided into at least two segments to ensure a uniform pressure distribution in the incoming-air duct.

The CT system of at least one embodiment comprises a gantry housing in which the gantry is arranged. The gantry has a rotatable support on which a plurality of system components of the CT system is arranged. These system components are primarily at least one radiator-detector system and further electronic components.

The cooling system comprises at least one air duct. An air duct is designed as an incoming-air duct for conveying the cold fresh or cooling air. A further air duct is designed as a waste-air duct for the removal of air heated during cooling of the system components.

According to at least one embodiment of the invention, the incoming-air duct of the cooling system is divided into at least two segments. In one embodiment, the incoming-air duct is divided into exactly two segments. In a further embodiment the incoming-air duct is divided into more than two, by way of example three, four or five, segments.

The at least two segments are preferably each individually supplied with air, i.e. are decoupled from each other. In other words, the air flows in the segments are not connected to each other, so no interactions occur between them. The segments of the incoming-air duct are preferably then connected in parallel, i.e. the entire incoming air flow is distributed among the plurality of segments.

The segments are connected to a shared incoming air supply. The segments advantageously have at least one inlet opening each, through which the incoming air flows into the individual segments. In one embodiment a segment has exactly one inlet opening. Other embodiments have segments with more than one inlet opening, by way of example two or more.

The pressure and thus the volume flow in the segments can preferably be adjusted by the size of the inlet openings in each case. On the one hand, the larger the inlet opening is, the greater the volume flow is in the segment. On the other hand, the lower the flow speed is in the segments, the greater the pressure is. Therefore, in order to reduce the pressure the inlet openings are advantageously reduced in size, and vice versa.

The flow speed of the air in the segments is greatest immediately behind the inlet opening(s). In the case of a segment with just one inlet opening the flow speed decreases during passage through the segment, so the pressure increases as the distance from the inlet opening increases.

In one embodiment of a segment with two inlet openings, the inlet openings can be arranged on the segment so as to oppose each other. The inlet openings are each arranged for example on the opposing ends, i.e. on a leading end and on a trailing end of the segment, viewed in the flow direction. A segment of this kind is designed for example in a C shape. The inlet openings are preferably each formed on the ends of the C legs. The air then flows from the two C legs toward each other, so the flow speed is at its lowest and the pressure is at its greatest at the point where the opposing air flows meet.

In a further embodiment a plurality of inlet openings of a segment may also be arranged side by side.

The shape of the individual segments is advantageously different, in particular the segments are arranged in different ways in the gantry. Shape and course of the segment can be adjusted using flow simulations in order to achieve the desired pressure ratios. One embodiment of the incoming-air duct provides for the segments to be arranged at least in part concentrically to each other.

The at least two segments are advantageously connected to the waste-air duct by the components to be cooled. Once the incoming air has passed through the inlet openings into the individual segments, it flows out of the incoming-air duct via a large number of air inlets into the gantry, where it flows through and cools the system components. From there the heated waste air passes through air outlets into the waste-air duct.

The air inlets in the system components on the gantry are advantageously arranged over the entire length of the individual segments. More than one segment can be associated with one air inlet, i.e. the air from a plurality of segments can flow into a system component through a shared air inlet. The pressure along the circumference of the gantry can be adjusted to a uniform value by the improved and simplified pressure adjustment, so the air always flows out of the segments into the rotating part of the gantry at constant pressure.

Air-impermeable partitions are advantageously arranged between the segments, and these separate the segments from each other. The rigidity of the structure of the entire incoming-air duct is also advantageously increased by the partitions.

The gantry cooling system can have different designs. In one embodiment the cooling system has an air cooling system. Here the hot waste air is given off to the surroundings of the CT system, by way of example an examination room, so the waste air is cooled again by an air conditioning unit of the building. The cooling circuit is open in this case. In a further embodiment the cooling system has a water cooling system. The cooling circuit is closed in this embodiment. The hot waste air is cooled again for example by means of a cooling unit such as a heat exchanger.

FIG. 1 shows an example CT system C1. The CT system C1 comprises a gantry housing C6 in which a gantry (not shown in greater detail here) having a rotatable support is located, to which a first X-ray tube C2 having an opposing first detector C3 is secured. A second X-ray tube C4 having a second opposing detector C5 is optionally provided. The CT system C1 also has a cooling system for removing the waste heat from the electrical components out of the gantry housing C6, see FIGS. 2 to 7.

A patient C7 is located on an examination table C8 which can be moved in the direction of the system axis C9, and with which he can be pushed continuously or sequentially during the scan with the X-ray radiation along the system axis C9 through a measuring field between the X-ray tubes C2 and C4 and the respectively associated detectors C3 and C5. This process is controlled by an arithmetic and control unit C10 with the aid of computer programs Prg1 to Prgn.

Figure 2:
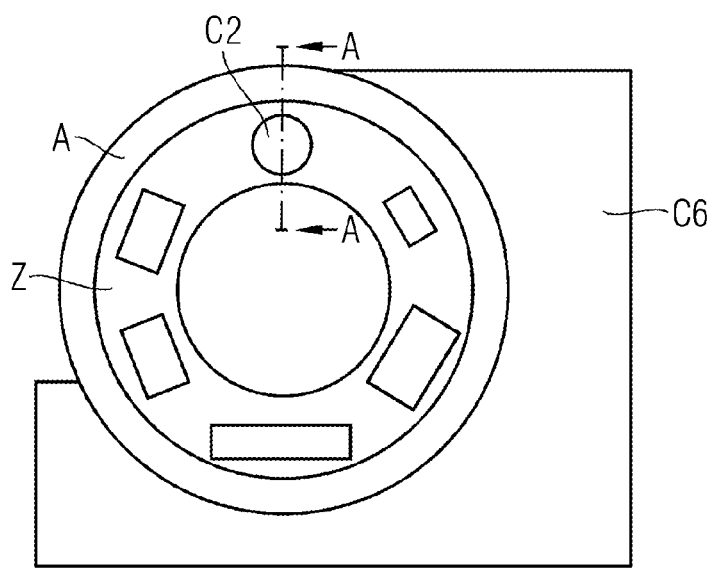
FIG. 2: shows a schematic view of a gantry housing.

FIG. 2 shows a schematic view of a known example gantry housing C6. A plane of intersection A-A extends through the gantry housing C6 and the X-ray tube C2 attached to the support. The air ducts of the cooling system of the CT system are also shown. The known cooling system comprises an incoming-air duct Z for introducing cold fresh air. The cooling system also comprises a waste-air duct A for removing the air heated by the system components on the support 1.

Figure 3:
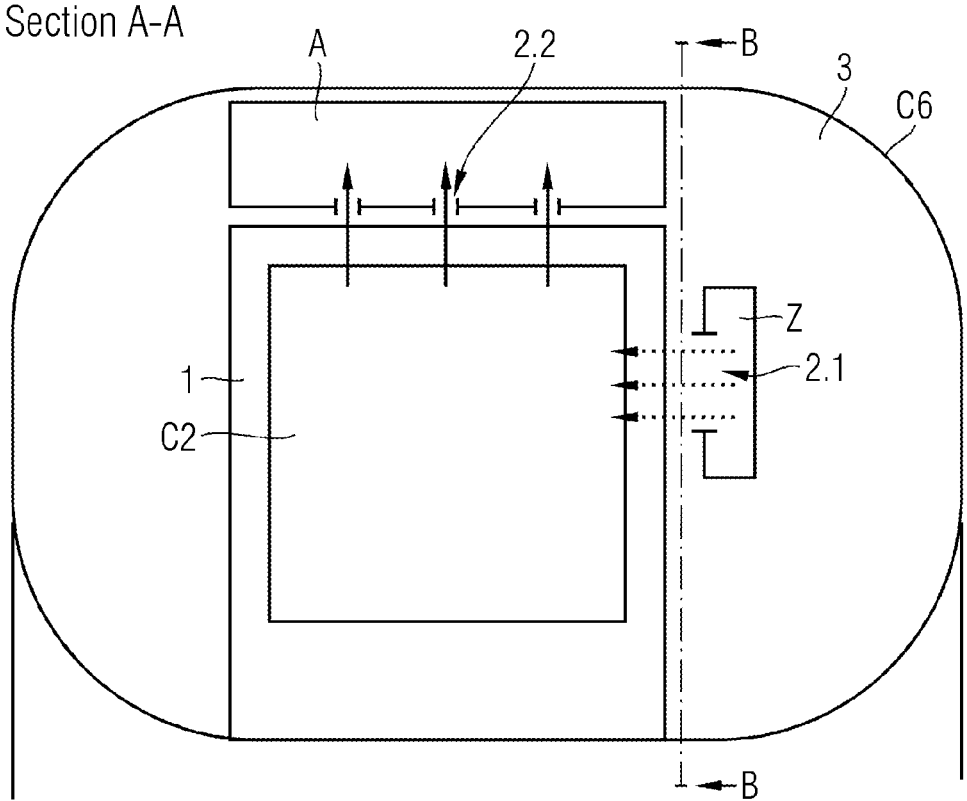
FIG. 3: shows a schematic view of the gantry housing according to FIG. 2 along a plane of intersection A-A.

FIG. 3 shows a schematic cross-section along the plane of intersection A-A through the gantry housing C6 known per se. The plane of intersection A-A extends through the X-ray tube C2 arranged on a rotatable support 1 of the gantry. The air flows through an air inlet 2.1 out of the incoming-air duct Z into the system components, therefore inter alia also into the X-ray tube C2 shown here, and flows through this. As it continues, the now heated air flows through air outlets 2.2 out of the system components into the waste-air duct A. As it passes through the X-ray tube C2 the air absorbs the waste heat thereof and therefore cools it. The course of the colder incoming air is symbolically illustrated here as broken-line arrows and the course of the hotter waste air as solid-line arrows.

Figure 4:
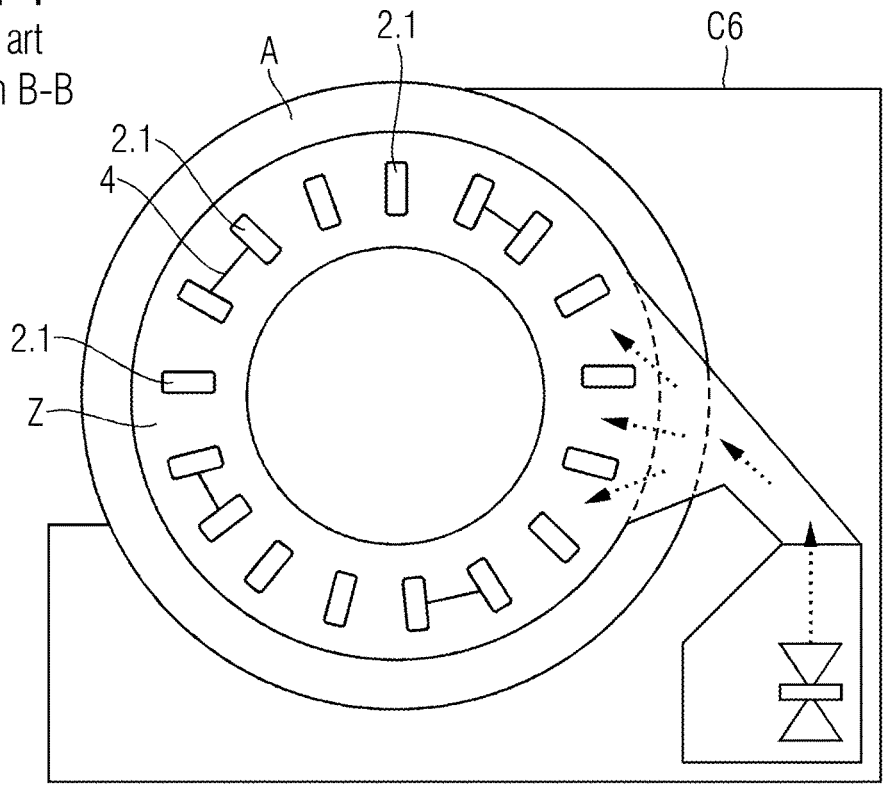
FIG. 4: shows a schematic view of the air circuit in the gantry according to FIG. 2 along a plane of intersection B-B.

FIG. 4 shows a schematic view of the air circuit in the gantry according to FIG. 2 along a plane of intersection B-B. The plane of intersection B-B divides the gantry housing C6 parallel to a plane perpendicular to the system axis C9 and extends according to FIG. 3 between the incoming-air duct Z and the waste-air duct A. In the region of the air intake into the incoming-air duct Z the waste-air duct A is arranged in a different drawing plane to the incoming-air duct Z and is therefore shown with a broken line. For a better overview an illustration of the system components on the support that are to be cooled has been omitted. The cooling system shown by way of example and known from the prior art has an air cooling system.

The air inlets 2.1 out of the incoming-air duct Z into the system components are also shown in this view. The air inlets 2.1 are uniformly spaced apart here and are arranged along the entire circumference of the gantry. For local pressure correction and to achieve optimally uniform cooling along the circumference of the gantry a plurality of baffles 4 are arranged in the incoming-air duct Z between the air inlets 2.1.

Figure 5:
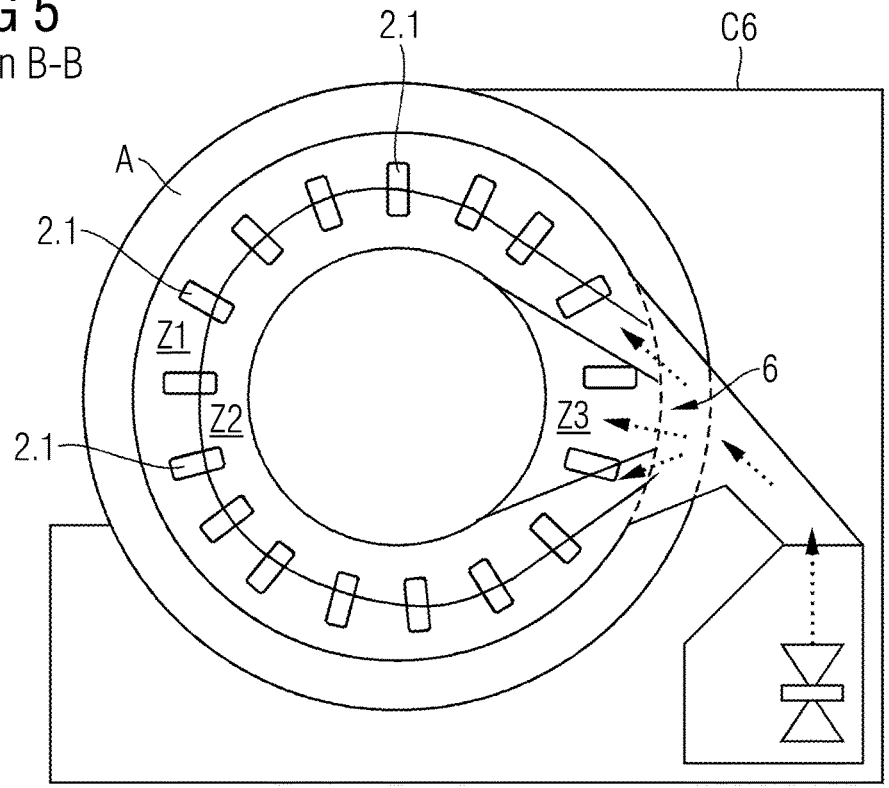
FIG. 5: shows a schematic view of the gantry according to FIG. 2 with an embodiment of an inventive air circuit along the plane of intersection B-B.

FIGS. 5 to 7 each show a schematic view of the gantry according to FIG. 2 along the plane of intersection B-B with different embodiments of the inventive air circuit. Basically the gantry and the cooling system correspond to FIGS. 5 to 7 of the embodiment shown in FIG. 4. Only the differences from the prior art and the details essential to the invention will be discussed below therefore. Identical components are identified by identical reference characters.

According to an embodiment of the invention the incoming-air duct Z is divided into a plurality of segments Z1 to Z4. The individual segments Z1 to Z4 are separated from each other by air-impermeable partitions 5. All segments Z1 to Z3 are constructed independently of each other, i.e. are not connected to each other. In the embodiments in FIGS. 5 to 7 the segments Z1 to Z4 each have a different design.

The segments Z1 to Z4 each have at least one inlet opening 6 through which the cold incoming air flows into the segments Z1 to Z4. The incoming air flows in parallel through the segments Z1 to Z3. The pressure in the segments Z1 to Z4 is individually adjusted. The size of the inlet opening(s) 6 can be varied for this purpose.

In the embodiment shown in FIG. 5, the incoming-air duct Z is divided into three segments Z1, Z2 and Z3. The two segments Z1 and Z2 are designed approximately in the shape of a C and are arranged in part concentrically. The third, middle segment Z3 is designed approximately in the shape of a truncated cone.

The two C-shaped segments Z1 and Z2 each have an inlet opening 4 at the ends of the C legs, through which the cold incoming air flows. The truncated cone-shaped, smallest segment Z3 has just one inlet opening 6. By adjusting the sizes of the inlet openings 6 a virtually uniform pressure is achieved over the entire length of the segments Z1 to Z3, so the air flows along the entire circumference of the gantry at uniform pressure into the cooled system components and cools the system components independently of position. This cooling process is ensured during rotation of the support and also when it is stationary.

FIG. 6 shows a further embodiment of the inventive air circuit. The incoming-air duct Z is divided here into four segments Z1 to Z4. An outermost C-shaped segment Z1 and two symmetrically arranged, bent segments Z2 and Z3 and one middle, truncated cone-shaped segment Z4 are formed.

The segment Z1 has two inlet openings 6, i.e. one inlet opening 6 on one end of the C leg respectively. The further segments Z2 to Z4 have just one inlet opening 6.

The air flows from the two opposing ends into the outermost C-shaped segment Z1. Strong eddies consequently result in a central region of the segment Z1, here opposite the inlet openings 6, if the air flows collide. As a result it is more difficult to adjust a uniform pressure in this segment Z1 than in the remaining segments Z2 to Z4.

FIG. 7 shows a further embodiment. Here the C-shaped segment Z1 is divided by a further partition 5 into two segments Z1.1 and Z1.2. The two segments Z1.1 and Z1.2 are separate and can be adjusted independently of each other.

Although the invention has been illustrated and described in more detail by the preferred example embodiment, it is not restricted by the disclosed examples and a person skilled in the art can derive other variations herefrom without departing from the scope of the invention.

What is claimed is:

1. A CT system for generating tomographic recordings of an examination object, comprising:
   a gantry, including a rotatable support, on which components of the CT system are arranged; and
   a cooling system for cooling the components arranged on the gantry with at least one incoming air duct being divided into at least two segments separated from each other by an air-impermeable partition to ensure a uniform pressure distribution in the at least one incoming-air duct.

2. The CT system of claim 1, wherein the at least two segments are each individually supplied with air.

3. The CT system of claim 1, wherein the at least two segments each include at least one respective inlet opening.

4. The CT system of claim 1, wherein the at least two segments are arranged at least in part concentrically to each other.

5. The CT system of claim 3, wherein pressure in the at least two segments are respectively adjustable by way of a size of the at least one inlet opening.

6. The CT system of claim 1, wherein partitions are arranged between the at least two segments.

7. The CT system of claim 1, wherein the at least two segments are connected to a waste-air duct by the components to be cooled.

8. The CT system of claim 1, wherein the cooling system includes an air cooling system.

9. The CT system of claim 1, wherein the cooling system includes a fluid cooling system.

10. The CT system of claim 4, wherein pressure in the at least two segments are respectively adjustable by way of a size of the at least one inlet opening.

11. The CT system of claim 2, wherein the at least two segments are arranged at least in part concentrically to each other.

12. The CT system of claim 2, wherein partitions are arranged between the at least two segments.

13. The CT system of claim 2, wherein the at least two segments are connected to a waste-air duct by the components to be cooled.

14. The CT system of claim 2, wherein the cooling system includes an air cooling system.

15. The CT system of claim 2, wherein the cooling system includes a fluid cooling system.

16. The CT system of claim 1, wherein the at least two segments are separated from each other by the air-impermeable partitions throughout the at least two segments.

* * * * *